United States Patent [19]

Miyata et al.

[11] 4,227,008
[45] Oct. 7, 1980

[54] PROCESS FOR PREPARING AROMATIC URETHANES

[75] Inventors: Katsuharu Miyata; Makoto Aiga; Seiji Hasegawa, all of Omuta, Japan

[73] Assignee: Mitsui Toatsu Chemicals, Incorporated, Tokyo, Japan

[21] Appl. No.: 927,779

[22] Filed: Jul. 25, 1978

[30] Foreign Application Priority Data

Jul. 25, 1977 [JP] Japan ................... 52-88440

[51] Int. Cl.$^2$ ........................................... C07C 125/04
[52] U.S. Cl. ........................................ 560/25; 560/24; 560/26
[58] Field of Search .................... 560/25, 24, 26

[56] References Cited

U.S. PATENT DOCUMENTS

| | | | |
|---|---|---|---|
| 3,338,956 | 8/1967 | Mountfield | 560/25 |
| 3,531,512 | 9/1970 | Hardy | 560/25 |
| 3,993,685 | 11/1976 | Zajacek et al. | 560/25 |

*Primary Examiner*—G. T. Breitenstein
*Attorney, Agent, or Firm*—Fisher, Christen & Sabol

[57] ABSTRACT

Aromatic urethanes can be produced by interacting an aromatic primary amino compound having a nitro group, a nitroso group or a carbamate group, an organic compound having at least one hydroxyl group, and carbon monoxide in the presence of a catalytic system composed of a platinum group metal and/or a compound thereof serving as catalyst and a Lewis acid and/or a compound thereof as promoter under high temperature and high pressure conditions. For instance, the interaction of 2-amino-4-nitrotoluene, ethanol and carbon monoxide in the presence of palladium chloride and a ferrous chloride-pyridine complex under high temperature and high pressure conditions can yield 2,4-diethylcarbamatetoluene.

14 Claims, No Drawings

4,227,008

PROCESS FOR PREPARING AROMATIC URETHANES

BACKGROUND OF THE INVENTION

1. Field of the Invention

This invention relates to a novel process for preparing an aromatic urethane compound. More particularly, it relates to a process for preparing an aromatic urethane from an aromatic primary amino compound having a nitro group, a nitroso group or a carbamate group, an organic compound containing at least one hydroxyl group, and carbon monoxide.

2. Description of the Prior Art

There have been recently proposed a large number of processes for producing aromatic urethanes from aromatic nitro compounds, organic compounds containing at least one hydroxyl group (hereinlater referred to simply as hydroxyl group-containing compound), and carbon monoxide in the presence of catalysts.

For example, U.S. Pat. No. 3,338,956 describes a process using rhodium chlorocarbonyl as a catalyst for the urethanation reaction. Further, British Pat. No. 1,543,051 discloses a process with which the urethanation reaction is conducted in rhodium chlorocarbonyl as the catalyst and a multi-valent metal halide as the promoter. In these processes, however, aromatic nitro compounds are essentially used as a principal starting material to permit the nitro group or groups to take part in the urethanation reaction.

As a result of an extensive study of a process of producing aromatic urethanes, we have found a hitherto unknown, really novel process for producing aromatic urethanes in which the urethanes can be produced from aromatic primary amine compounds, carbon monoxide and hydroxyl group-containing compounds.

SUMMARY OF THE INVENTION

It is accordingly an object of the present invention to provide a novel process for producing aromatic urethanes in which aromatic primary amino compounds which have never been used as the starting material for producing aromatic urethanes are used to react with hydroxyl group-containing compounds and carbon monoxide.

The above object can be achieved by a process for producing aromatic urethanes which comprises interacting an aromatic primary amino compound having a nitro group, a nitroso group or a carbamate group, a hydroxyl group-containing compound, and carbon monoxide in the presence of a catalytic system composed of a platinum group metal and/or a compound thereof and a Lewis acid and/or its complex under high temperature and high pressure conditions.

It is known that if amino compounds having a nitro group as a substituent are subjected to a urethanation reaction in the presence of the catalytic system indicated above, the nitro group can be converted into a carbamate. However, it can not be expected at all from prior art processes that the amino group is also convertible into a carbamate. It has been also found that where aromatic amino compounds which are free of a nitro group, a nitroso group or a carbamate group are used as the starting material, no urethanation reaction takes place. This is a hitherto unknown and rather amazing fact concerning the production of aromatic urethanes from aromatic primary amino compounds, carbon monoxide and hydroxyl group-containing compounds.

DESCRIPTION OF THE PREFERRED EMBODIMENTS

As mentioned hereinabove, the aromatic amino compounds which are employed as the chief starting material are aromatic primary amino compounds having a nitro group, a nitroso group or a carbamate group. Examples of such compounds include m- and p-nitroaniline, m- and p-nitrosoaniline, m- and p-carbamate-aniline, 2-amino-4-nitrotoluene, 2-amino-4-nitrosotoluene, 2-amino-4-carbamatetoluene, 2-nitro-4-aminotoluene, 2-nitroso-4-aminotoluene, 2-carbamate-4-aminotoluene, 2-amino-6-nitrotoluene, 2-amino-6-nitrosotoluene, 2-amino-6-carbamatetoluene, 4-amino-4'-nitrobiphenyl, 4-amino-4'-nitrosobiphenyl, 4-amino-4'-carbamatebiphenyl, 2-amino-4-nitrobiphenyl, 2-amino-4-nitrosobiphenyl, 2-amino-4-carbamatebiphenyl, 2-nitro-4-aminobiphenyl, 2-nitroso-4-aminobiphenyl, 2-carbamate-4-aminobiphenyl, 4-amino-4'-nitrodibenzyl, 4-amino-4'-nitrosodibenzyl, 4-amino-4'-carbamatedibenzyl, 4-amino-4'-nitrodiphenylmethane, 4-amino-4'-nitrosodiphenylmethane, 4-amino-4'-carbamatediphenylmethane, 4-amino-4'-nitrodiphenyl ether, 4-amino-4'-nitrosodiphenyl ether, 4-amino-4'-carbamatediphenyl ether, bis(2-amino-4-nitrophenyl) ether, bis(2-amino-4-nitrosophenyl) ether, bis(2-amino-4-carbamatephenyl) ether, bis(2-nitro-4-aminophenyl) ether, bis(2-nitroso-4-aminophenyl) ether, bis(2-carbamate-4-aminophenyl) ether, α-amino-α'-nitro-m-xylene, α-amino-α'-nitroso-m-xylene, α-amino-α'-carbamate-m-xylene, α-amino-α'-nitro-p-xylene, α-amino-α'-nitroso-p-xylene, α-amino-α'-carbamate-p-xylene, 1-chloro-2-amino-4-nitrobenzene, 1-chloro-2-amino-4-nitrosobenzene, 1-chloro-2-amino-4-carbamatebenzene, 1-chloro-2-nitro-4-aminobenzene, 1-chloro-2-nitroso-4-aminobenzene, 1-chloro-2-carbamate-4-aminobenzene, 1-amino-5-nitronaphthalene, 1-amino-5-nitrosonaphthalene, 1-amino-5-carbamatenaphthalene and the like. The isomers or homologues of these aromatic amino compounds are also usable. These aromatic amino compounds may be used singly or in combination. It will be noted that the nitro group of aromatic nitro compounds are also converted into a corresponding urethane under reaction conditions used in the practice of the invention. Of the abovementioned amino compounds, nitroaminotoluenes and aminocarbamatetoluenes are most preferable because these compounds are more reactive than the others.

The hydroxyl group-containing compounds useful in the process of the invention include primary, secondary and tertiary monohydric alcohols and polyhydric alcohols, and monohydric phenols and polyhydric phenols. Typical of such compounds are ethanol and phenol. Suitable alcohols may be expressed by $R(OH)_n$ in which R represents a linear or branched alkyl, a cycloalkyl, an alkylene, a cycloalkylene or an aralkyl, and n is an integer of 1 or 2 or more. These alcohols may further include a substituent containing an oxygen, nitrogen, halogen or sulfur atom such as, for example, halogen, sulfoxide, sulfon, amide, carbonyl or a carboxylic acid ester group.

Examples of the alcohols expressed by $R(OH)_n$ include monohydric alcohols such as methyl alcohol, ethyl alcohol, n- and iso-propyl alcohol, n-, iso- and t-butyl alcohol, linear or branched amyl alcohol, hexyl alcohol, cyclohexyl alcohol, lauryl alcohol, cetyl alcohol, benzyl alcohol, chlorobenzyl alcohol, methoxylbenzyl alcohol, etc., dihydric alcohols such as ethylene glycol, diethylene glycol, propylene glycol, dipropylene glycol, etc., trihydric alcohols such as glycerol, hexanetriol, etc., and more polyfunctional polyols.

Suitable examples of the phenols include phenol, chlorophenol, cresol, ethylphenol, linear or branched propylphenol, butyl- and higher alkylphenols, catechol, resorcin, 4,4'-dihydroxydiphenylmethane, 2,2'-isopropylidenediphenyl, anthranol, phenanthrol, pyrogallol, phloroglucinol, etc. Of these, methanol, ethanol and isobutanol are preferred since the use of these alcohols results in higher velocities of reaction and higher yields of final product.

The platinum group metals and/or compounds thereof which are used as a chief catalyst in the process of the invention are palladium, rhodium and ruthenium elements or compounds thereof, or a mixture thereof. More particularly, examples of these elements and compounds are palladium, rhodium, ruthenium elements, their compounds such as halides, cyanides, thiocyanides, isocyanides, oxides, sulfates, nitrates, carbonyl compounds, etc., their addition compounds or complexes with tertiary amines such as triethylamine, pyridine, isoquinoline, etc., and their complexes with organic phosphorous compounds such as triphenylphosphine. These catalysts may be used for the reaction as they are or may be supported on carriers such as of alumina, silica, carbon, barium sulfate, calcium carbonate, asbestos, bentonite, diatomaceous earth, fuller's earth, organic ion-exchange resins, inorganic ion-exchange resins, magnesium silicate, aluminium silicate, molecular sieve and the like. These carriers may be charged into a reactor separately from palladium, rhodium, ruthenium or their compounds. In view of a great catalytic activity, palladium and/or its compounds are preferable to other platinum group metals or compounds thereof.

The Lewis acids and/or compounds thereof are used as the promoter. The term "Lewis acids" herein used is intended to imply those as described, for example, in Physical Organic Chemistry by Jack Hine, 1962 (McGrowHill Book Co., New York), including Brönsted acids.

Examples of such acids include halides, sulfates, acetates, phosphates, nitrates such as of tin, titanium, germanium, aluminium, iron, nickel, zinc, cobalt, manganese, thallium, zirconium, copper, lead, vanadium, niobium, tantalum, mercury, etc. More particularly, suitable Lewis acids include ferric chloride, ferrous chloride, stannic chloride and copper acetate. Of these, ferrous chloride and ferric chloride are most preferable. Further, the compounds of the Lewis acids may be, for example, complexes with tertiary amines or organic phosphorous compounds. Examples of such tertiary amines capable of producing complexes include triethylamine, N,N-diethylaniline, N,N-diethylcyclohexylamine, 1,4-diazabicyclo-[2,2,2]octane, and nitrogen-containing aromatic heterocyclic compounds such as pyridine, quinoline and isoquinoline. Examples of the phosphorous compounds or phosphines include triphenylphosphine, dimethylphenylphosphine, bisdiphenylphosphinoethane and the like. Of these complexes, complexes of ferrous chloride and nitrogen-containing aromatic heterocyclic compounds are preferred since they are less corrosive against a reactor, can improve the yield of a final product, and permit easier recovery of the catalyst as compared with other promoters.

These complex compounds serve more effectively when used after preparation of the complexes but the starting materials for such complexes may be introduced into the reaction system separately.

If a nitrogen-containing aromatic heterocyclic compound is used, aside from the Lewis acid, as the promoter in the reaction system, addition of water in small amount will facilitate the reaction to proceed at a much higher velocity.

It is desirable that the reaction is conducted using the hydroxyl group-containing organic compound and carbon monoxide in such amounts that the hydroxyl group and carbon monoxide are in at least equimolar or greater ratios to the amino group in the case of an amino compound having a carbamate group and to a total of the amino group and the nitro or nitroso group in the case of an amino compound having a nitro or nitroso group.

The amount of the platinum group metal may widely vary depending on the kind of the amino compound and other reaction conditions but is generally in the range of $1-1\times10^{-5}$, preferably $5\times10^{-1}-1\times10^{-4}$, as metal element, by weight ratio to the amino compound.

The Lewis acid used as the promoter is used in the range of $2-2\times10^{-3}$, preferably $1-5\times10^{-2}$, by weight ratio to the amino compound.

The reaction temperature is generally maintained in the range of 80°–230° C., preferably 140°–200° C. The reaction pressure is in the range of 10–1000 kg/cm$^2$G, preferably 30–500 kg/cm$^2$G as expressed in terms of the partial pressure of carbon monoxide. Addition of a small amount of water will shorten the reaction time. In this case, the amount of water added is in the range of 1–70 moles, preferably 10–50 moles per mole of the starting aromatic primary amine. Amounts less than 1 mole of water per mole of the amino compound does not give an appreciable effect on the reaction time, whereas the larger amount lowers the yield of a final product.

The reaction time depends on the property or kind of the amino compound, reaction temperature, reaction pressure, the kind and amount of the catalyst, amount of water and the type of reactor but is generally in the range of 5 minutes to 6 hours.

After completion of the reaction, the reaction mixture is cooled. After discharging the gas from the reaction system, the reaction product is subjected to a treatment by an ordinary separation technique such as filtration, distillation or other suitable means thereby separating the resulting urethane from unreacted materials, by-products, the solvent and catalyst.

The present invention will be particularly illustrated by way of the following examples, which should not be construed as limiting thereto the present invention. In the examples, all of the reactions were effected in a stainless steel (SUS 32), magnetically agitated autoclave.

EXAMPLE 1

10.33 g of 2-amino-4-nitrotoluene, 68 ml of ethanol, 0.0086 g of palladium chloride, 3.71 g of the ferrous chloride-pyridine complex (obtained by interacting ferrous chloride and pyridine in a 1:2 molar ratio of ferrous chloride: pyridine with methanol serving as solvent), and 0.29 g of water were charged into the autoclave with an inner volume of 200 ml. The air in the autoclave was replaced by nitrogen gas. Then, carbon monoxide was charged into the autoclave under pressure until the initial pressure reached 90 kg/cm²G. The reaction system was heated under agitation and subjected to the reaction at 165° C. for 40 min. After completion of the reaction, the system was allowed to cool to room temperature and, after degassing, the reaction solution was analyzed, revealing that the yield of 2,4-diethylcarbamate toluene (hereinlater referred to simply as diurethane) was 84.6%.

EXAMPLE 2

7.8 g of 2-amino-4-ethylcarbamatetoluene, 6.0 ml of ethanol, 0.02 g of palladium chloride, and 8.8 g of ferrous chloride-pyridine complex were charged into the autoclave with an inner volume of 200 ml. Carbon monoxide was charged into the reaction system until the initial pressure reached 70 kg/cm²G to undergo the reaction at 160° C. for 240 minutes. After completion of the reaction, the reaction solution was analyzed, with the result that the yield of the diurethane was 20%.

COMPARATIVE EXAMPLE 1

6.3 g of aniline, 68 ml of ethanol, 0.02 g of palladium chloride, and 7.42 g of ferrous chloride-pyridine complex were charged into the autoclave with an inner volume of 200 ml, followed by the urethanation reaction under an initial pressure of carbon monoxide of 90 kg/cm²G at 165° C. for 240 minutes. After completion of the reaction, the reaction solution was analyzed, with the result that no N-phenylethylcarbamate was recognized.

EXAMPLES 3-8

Various amino compounds other than 2-amino-4-ethylcarbamatetoluene were used to conduct the urethanation reaction in the same manner as in Example 1 using the initial pressure of 90 kg/cm²G, the reaction temperature of 165° C. and other reaction parameters indicated in Table below. The results are also shown in the Table.

ing aromatic heterocyclic compound or with an organic phosphorus compound under high temperature and high pressure conditions.

2. A process according to claim 1, wherein said aromatic primary amino compound is a nitroaminotoluene.

3. A process according to claim 1, wherein said aromatic primary amino compound is an aminocarbamatetoluene.

4. A process according to claim 1, wherein said catalyst is palladium chloride.

5. A process according to claim 1, wherein said Lewis acid is ferrous chloride.

6. A process according to claim 1, wherein said Lewis acid is ferric chloride.

7. A process according to claim 1, wherein water is added to the reaction system in an amount of 1-70 mole % per mole of the starting aromatic primary amino compound.

8. A process according to claim 7, wherein said complex is a complex of ferrous chloride with a nitrogen-containing aromatic heterocyclic compound.

9. A process according to claim 1 wherein said catalyst system is composed of metallic palladium and/or a compound thereof and a complex of ferrous chloride with a nitrogen-containing aromatic heterocyclic compound.

10. A process according to claim 1 wherein the reaction temperature is in the range of 80° C. to 230° C. and the reaction pressure is in the range of 10 to 1000 kg/cm²G.

11. A process according to claim 1 wherein said catalyst is metallic palladium or a palladium compound selected from the group consisting of palladium halide, cyanide, thiocyanide, isocyanide, oxide, sulfate, nitrate, palladium carbonyl compounds, complexes of palladium with triethylamine, pyridine, isoquinoline, and triphenylphosphine.

12. A process according to claim 9 wherein said nitrogen-containing aromatic heterocyclic compound is selected from the group consisting of pyridine, quinoline, and isoquinoline.

TABLE

| Example No. | Amino Compound | Amount (g) | Alcohol | Amount (ml) | Water (g) | PdCl$_2$ (g) | FeCl$_2$-(pyridine)$_2$ (g) | Reaction time (min) | Yield of diurethane (%) |
|---|---|---|---|---|---|---|---|---|---|
| 3 | m-nitroaniline | 9.7 | ethanol | 68 | 0.27 | 0.008 | 2.2 | 40 | 85 |
| 4 | p-nitroaniline | 9.7 | " | " | " | " | " | " | 80 |
| 5 | m-ethylcarbamate-aniline | 12.5 | " | " | 0 | 0.032 | 6.3 | 240 | 20 |
| 6 | 4-amino-2-nitrotoluene | 10.7 | " | " | 0.30 | 0.009 | 2.5 | 40 | 85 |
| 7 | 4-amino-2-ethylcarbamate-toluene | 13.6 | " | " | 0 | 0.035 | 6.8 | 240 | 20 |
| 8 | 2-amino-4-isobutylcarbamate-toluene | 15.6 | isobutanol | " | 0 | 0.040 | 7.8 | 240 | 30 |

What is claimed is:

1. A process for producing an aromatic urethane comprising interacting an aromatic primary amino compound having a nitro group, a nitroso group or a carbamate group, an organic compound having at least one hydroxyl group, and carbon monoxide in the presence of a catalytic system comprising a palladium catalyst and a complex of a Lewis acid with a nitrogen-contain- 13. A process according to claim 1, wherein said organic phosphorous compound is selected from the group consisting of triphenylphosphine, dimethylphenylphosphine and bisdiphenylphosphinoethane.

14. A process according to claim 1, wherein said complex is a ferrous chloride-pyridine complex.

* * * * *